United States Patent
Faltys et al.

(10) Patent No.: US 9,855,425 B2
(45) Date of Patent: Jan. 2, 2018

(54) INFORMATION PROCESSING AND STORAGE IN A COCHLEAR STIMULATION SYSTEM

(71) Applicant: Advanced Bionics AG, Staefa (CH)

(72) Inventors: Michael A. Faltys, Northridge, CA (US); Timothy J. Starkweather, Simi Valley, CA (US); Anthony K. Arnold, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 22 days.

(21) Appl. No.: 14/453,148

(22) Filed: Aug. 6, 2014

(65) Prior Publication Data
US 2014/0350641 A1    Nov. 27, 2014

Related U.S. Application Data

(63) Continuation of application No. 11/418,847, filed on May 5, 2006, now Pat. No. 8,818,517.

(51) Int. Cl.
*A61N 1/05* (2006.01)
*A61N 1/36* (2006.01)
*A61N 1/372* (2006.01)

(52) U.S. Cl.
CPC ..... *A61N 1/36032* (2013.01); *A61N 1/36036* (2017.08); *A61N 1/37252* (2013.01); *A61N 1/37264* (2013.01)

(58) Field of Classification Search
CPC ............ A61N 1/36032; A61N 1/37264; A61N 1/37252; A61N 1/0541
See application file for complete search history.

(56) References Cited

U.S. PATENT DOCUMENTS

| 3,751,605 A | 8/1973 | Michelson |
| 4,051,330 A | 9/1977 | Cole |

(Continued)

FOREIGN PATENT DOCUMENTS

| WO | 96/34508 A1 | 10/1996 |
| WO | 96/39005 A1 | 12/1996 |

(Continued)

OTHER PUBLICATIONS

Rubinstein et al., "The Neurophysiological Effects of Simulated Auditory Prosthesis Simulation" Second Quarterly Progress Report: NO1-DC-6-2111 (May 27, 1997). (Previously cited in parent case, U.S. Appl. No. 11/418,847).

(Continued)

*Primary Examiner* — Tammie K Heller
(74) *Attorney, Agent, or Firm* — Blank Rome, LLP

(57) ABSTRACT

Information can be stored in a cochlear stimulation system by determining an item of patient specific information, transferring the item of patient specific information to an implantable portion of the cochlear stimulation system, and permanently storing the item of patient specific information in the implantable portion of the cochlear stimulation system. The item of patient specific information can comprise a parameter for use in generating a stimulation current. The implantable portion of the cochlear stimulation system also can be configured to permanently store one or more items of patient specific information in an alterable fashion. Further, an item of patient specific information can be retrieved from the implantable portion of the cochlear stimulation system. Additionally, an item of non-patient specific information for use in processing a received acoustic signal can be determined and permanently stored in an external portion of the cochlear stimulation system.

18 Claims, 7 Drawing Sheets

(56) References Cited

U.S. PATENT DOCUMENTS

| | | | |
|---|---|---|---|
| 4,400,590 A | 8/1983 | Michelson |
| 4,495,384 A | 1/1985 | Scott et al. |
| 4,612,934 A | 9/1986 | Borkan |
| 4,793,353 A | 12/1988 | Borkan |
| 4,819,647 A | 4/1989 | Byers et al. |
| 5,033,090 A | 7/1991 | Weinrich |
| 5,201,006 A | 4/1993 | Weinrich |
| 5,204,917 A | 4/1993 | Arndt et al. |
| 5,357,576 A | 10/1994 | Arndt |
| 5,597,380 A | 1/1997 | McDermott et al. |
| 5,601,617 A | 2/1997 | Loeb et al. |
| 5,603,726 A | 2/1997 | Schulman et al. |
| 5,626,629 A | 5/1997 | Faltys et al. |
| 5,845,332 A * | 12/1998 | Inoue ............... G06F 12/1441 |
| | | | 365/195 |
| 5,938,691 A | 8/1999 | Schulman et al. |
| 6,002,966 A | 12/1999 | Loeb et al. |
| 6,067,474 A | 5/2000 | Schulman et al. |
| 6,078,838 A | 6/2000 | Rubinstein |
| 6,129,753 A | 10/2000 | Kuzma |
| 6,154,678 A | 11/2000 | Lauro |
| 6,157,861 A | 12/2000 | Faltys et al. |
| 6,195,585 B1 | 2/2001 | Karunasiri et al. |
| 6,198,971 B1 | 3/2001 | Leysieffer |
| 6,205,360 B1 | 3/2001 | Carter et al. |
| 6,208,882 B1 | 3/2001 | Lenarz et al. |
| 6,216,045 B1 | 4/2001 | Black et al. |
| 6,219,580 B1 | 4/2001 | Faltys et al. |
| 6,272,382 B1 | 8/2001 | Faltys et al. |
| 6,289,247 B1 | 9/2001 | Faltys et al. |
| 6,295,467 B1 | 9/2001 | Kollmeier et al. |
| 6,308,101 B1 | 10/2001 | Faltys et al. |
| 6,415,185 B1 | 7/2002 | Maltan |
| 6,522,764 B1 | 2/2003 | Bogeskov-Jensen |
| 6,584,356 B2 * | 6/2003 | Wassmund ............ A61N 1/362 |
| | | | 607/30 |
| 6,658,125 B1 | 12/2003 | Batting |
| 6,697,674 B2 | 2/2004 | Leysieffer |
| 6,700,983 B1 | 3/2004 | Bogeskov-Jensen et al. |
| 6,728,578 B1 | 4/2004 | Voelkel |
| 6,775,389 B2 | 8/2004 | Harrison et al. |
| 6,778,858 B1 | 8/2004 | Peeters |
| 6,826,430 B2 | 11/2004 | Faltys et al. |
| 6,842,647 B1 | 1/2005 | Griffith et al. |
| 6,980,864 B2 | 12/2005 | Faltys et al. |
| 7,003,876 B2 | 2/2006 | Crawford et al. |
| 7,043,303 B1 | 5/2006 | Overstreet |
| 7,076,308 B1 | 7/2006 | Overstreet et al. |
| 7,110,823 B2 | 9/2006 | Whitehurst et al. |
| 7,200,504 B1 | 4/2007 | Fister |
| 7,203,548 B2 | 4/2007 | Whitehurst et al. |
| 7,242,985 B1 | 7/2007 | Fridman et al. |
| 7,248,926 B2 | 7/2007 | Woods et al. |
| 7,277,760 B1 | 10/2007 | Litvak et al. |
| 7,292,890 B2 | 11/2007 | Whitehurst et al. |
| 7,292,891 B2 | 11/2007 | Hartley et al. |
| 7,292,892 B2 | 11/2007 | Litvak et al. |
| 7,308,303 B2 | 12/2007 | Whitehurst et al. |
| 7,317,945 B2 | 1/2008 | Litvak et al. |
| 7,349,741 B2 | 3/2008 | Maltan et al. |
| 7,450,994 B1 | 11/2008 | Mishra et al. |
| 7,502,653 B2 | 3/2009 | Daly |
| 7,512,448 B2 | 3/2009 | Malick et al. |
| 7,522,961 B2 | 4/2009 | Fridman et al. |
| 7,599,500 B1 | 10/2009 | Segel et al. |
| 7,702,396 B2 | 4/2010 | Livtvak et al. |
| 7,729,758 B2 | 6/2010 | Haller et al. |
| 7,729,775 B2 | 6/2010 | Saoji et al. |
| 7,801,600 B1 | 9/2010 | Carbunaru et al. |
| 7,801,602 B2 | 9/2010 | McClure et al. |
| 7,822,480 B2 | 10/2010 | Park et al. |
| 7,860,570 B2 | 12/2010 | Whitehurst et al. |
| 7,889,539 B2 | 2/2011 | Rinerson et al. |
| 7,899,539 B2 | 3/2011 | Whitehurst et al. |
| 8,027,733 B1 | 9/2011 | Fridman et al. |
| 8,175,717 B2 | 5/2012 | Haller et al. |
| 8,265,765 B2 | 9/2012 | Nicolai et al. |
| 8,386,048 B2 | 2/2013 | McClure et al. |
| 2004/0015205 A1 | 1/2004 | Whitehurst et al. |
| 2004/0138723 A1 | 7/2004 | Malick et al. |
| 2004/0230254 A1 | 11/2004 | Harrison et al. |
| 2005/0058317 A1 * | 3/2005 | Montgomery ......... H04R 5/023 |
| | | | 381/376 |
| 2005/0102006 A1 | 5/2005 | Whitehurst et al. |
| 2005/0143781 A1 | 6/2005 | Carbunaru et al. |
| 2006/0100672 A1 | 5/2006 | Litvak |
| 2007/0123938 A1 | 5/2007 | Haller et al. |
| 2007/0135862 A1 * | 6/2007 | Nicolai .............. A61N 1/36032 |
| | | | 607/56 |
| 2010/0292759 A1 | 11/2010 | Hahn et al. |
| 2010/0331913 A1 | 12/2010 | Mann et al. |
| 2011/0040350 A1 | 2/2011 | Griffith |

FOREIGN PATENT DOCUMENTS

| | | |
|---|---|---|
| WO | 97/48447 A1 | 12/1997 |
| WO | 99/49815 A1 | 10/1999 |
| WO | 01/74278 A2 | 10/2001 |
| WO | 03/015863 A2 | 2/2003 |
| WO | 03/018113 A1 | 3/2003 |
| WO | 2004/043537 A1 | 5/2004 |
| WO | 2006/053101 A1 | 5/2006 |
| WO | 2007/030496 A1 | 3/2007 |

OTHER PUBLICATIONS van Wieringen, et al., "Comparison of Procedures to Determine Electrical Stimulation Thresholds in Cochlear Implant Users", Ear and Hearing, 22 (6): 528-538 (2001), pp. 528-538 (2001). (Previously cited in parent case, U.S. Appl. No. 11/418,847).

Zen, et al. "Loudness of Simple and Complex Stimuli in Electric Hearing", Annals of Otology, Rhinology & Laryngology, 104 (No. 9, Part 2, Suppl. 166): 235-238 (Sep. 1995). (Previously cited in parent case, U.S. Appl. No. 11/418,847).

Examiner's first report corresponding application No. 2007248343, dated Dec. 2, 2009: Viara Van Raad, Patent Examination A. (Previously cited in parent case, U.S. Appl. No. 11/418,847).

Australian Examiner's report No. 2 on corresponding application No. 2007248343, dated Feb. 24, 2010.

International Written Opinion received for corresponding PCT/US20071066794, dated Nov. 20, 20008.

\* cited by examiner

INFORMATION PROCESSING AND STORAGE IN A COCHLEAR STIMULATION SYSTEM

CROSS-REFERENCE TO RELATED APPLICATIONS

This is a continuation application of U.S. patent application Ser. No. 11/418,847, filed May 5, 2006, now U.S. Pat. No. 8,818,517, which is incorporated by reference, and to which priority is claimed.

BACKGROUND OF THE INVENTION

The present disclosure relates to implantable neurostimulator devices and systems, for example, cochlear stimulation systems, and to strategies for storing parameters employed in conjunction with such systems.

Prior to the past several decades, restoring hearing to the deaf was generally believed to be impossible. More recently, however, scientists have had increasing success in restoring normal hearing in subjects affected by substantial hearing loss. In some cases, hearing loss can be overcome through electrical stimulation. For example, electrical signals can be applied to the auditory nerve, bypassing damaged cochlear hair cells that may be disrupting hearing. Initial attempts to restore hearing using this type of technique were not very successful, because some patients were still unable to understand speech. Over time, however, the auditory sensations elicited by electrical stimulation gradually came closer to approximating normal speech. Electrical stimulation of the auditory nerve can be implemented through a prosthetic device, commonly referred to as a cochlear implant, which is surgically implanted into a subject affected by hearing loss.

Cochlear stimulation systems, such as the systems described in U.S. Pat. Nos. 5,938,691 and 6,219,580, each of which is incorporated herein by reference, produce sensations of sound in patients affected by hearing loss through direct stimulation of the ganglia of the auditory nerve cells. Cochlear stimulation systems are generally comprised of several components, including an electrode array that incorporates one or more electrode pairs, an implantable cochlear stimulator, an externally wearable speech processor (or signal processor) with one or more microphones, and a communication path that couples the external speech processor and the implantable cochlear stimulator through the skin, such as a radio frequency link. The external portion of the communication pathway can be incorporated into a headpiece that can be affixed and aligned with the implantable cochlear stimulator, such as through the use of one or more magnets. Alternatively, the external portion of the communication pathway can be integrated into the speech processor, which can be affixed adjacent to the pinna in proximity to the implantable cochlear stimulator.

The acoustic signals received by the one or more microphones included in the cochlear stimulation system are transformed into sound data by the speech processor. The sound data can then be transferred to the implantable cochlear stimulator, such as by transmission over the communication pathway. Once received in the implantable cochlear stimulator, the sound data can be used to selectively generate the electrical stimuli that are directed to one or more cochlea stimulating channels, each of which is associated with one or more electrodes or electrode pairs included within the electrode array.

Within the cochlea, there are two main cues that convey "pitch" (frequency) information to the listener. They are (1) the place or location of stimulation along the length of the cochlear duct and (2) the temporal structure of the stimulating waveform. Specific frequencies of sound are detected by specific portions of the cochlea, such that each frequency is mapped to a particular location along the cochlea. Generally, from low to high, sound frequencies are mapped from the apical to the basilar direction. Accordingly, the electrode array can be fitted to a patient to arrive at a mapping scheme such that electrodes near the base of the cochlea are stimulated with high frequency signals, while electrodes near the apex are stimulated with low frequency signals. Thus, the stimulation signals provided to the electrodes model the received acoustic signal associated with a particular frequency band.

Several different strategies have been developed for processing detected acoustic signals and transforming them into electrical stimuli that can be applied to the cochlea. These strategies, often referred to as speech processing strategies, define a pattern of electrical waveforms that can be applied as controlled electrical currents to the one or more cochlea stimulating channels associated with the electrode array. Speech processing strategies can be broadly classified as: (1) sequential or non-sequential pulsitile stimulation, in which only one electrode receives an electrical pulse at a time; (2) simultaneous pulsitile stimulation, in which substantially all of the electrodes receive electrical pulses at the same time, approximating an analog signal; or (3) partially simultaneous pulsitile stimulation, in which only a select grouping of electrodes receive electrical pulses at the same time and the electrical pulses are received in accordance with a predefined pattern.

It also is possible to further divided these strategies based on the waveform of the electrical stimuli, i.e., whether the electrical stimuli is an analog waveform or a biphasic (or multiphasic) waveform. Generally, analog waveforms represent filtered versions of a continuous acoustic signal, such as the signal received by a microphone. Analog waveforms are typically reconstructed by the generation of continuous, short, monophasic pulses or samples. The rate at which the samples are taken from a continuous acoustic signal must be high enough to permit the accurate reconstruction of the temporal details of the continuous acoustic signal. If an analog signal is not sampled at a sufficiently high rate, artifacts may result. Biphasic (or multiphasic) pulses, commonly referred to as pulsitile waveforms, typically include a single cycle of a square wave in which current flows in one direction at a particular magnitude and for a particular time, followed by a current flow in the opposite direction at a similar magnitude and for a similar period of time.

There are numerous other stimulation patterns known in the art that may be formulated. One simulation pattern may prove more effective for a particular patient than any other stimulation pattern, since each patient may respond differently to a particular speech processing strategy. The complex biophysical phenomenon associated with the electrical stimulation of neurons and psychophysical phenomena regarding the interpretation of neural activity by the auditory nervous system suggest that the quality and intelligibility of speech precepts evoked by a cochlear stimulation system may be improved in a given patient by more specific manipulations of the electrical stimuli tailored to that patient. Stimulation strategies are described in further detail in U.S. patent application Ser. No. 11/226,777, which is incorporated herein by reference. Identifying which of the available speech processing and stimulation strategies is most beneficial for a given patient is commonly performed at the fitting stage.

A specialist, such as an audiologist, generally customizes or "fits" a newly provided cochlear stimulation system to a patient. In fitting the cochlear stimulation system, the specialist selects the modes and methods of operation that will be used by the system to help the patient perceive sound. The modes and methods include information defining the general processing characteristics, such as parameters utilized by the speech processor. Additionally, the modes and methods include patient-specific information, such as stimulation parameters and settings. Although the specialist can exercise a substantial amount of control and discretion in selecting the modes and methods of operation, the specialist typically employs a fitting system to properly customize the cochlear stimulation system to meet the individual needs of a patient. Fitting systems are described in further detail in U.S. Pat. Nos. 5,626,629 and 6,289,247, both of which are incorporated herein by reference.

Once they have been determined, the modes and methods of operation can be stored in the cochlear stimulation system for use in configuring the device each time it is initialized, which generally occurs whenever the external portion of the unit is powered off or disconnected from the patient. During initialization, one or more items of information can be transmitted between the speech processor portion and the implantable cochlear stimulator. In the implantable cochlear stimulator, information can be stored in a random access memory for use during operation. For example, a speech processor can be configured to detect the presence of an implantable cochlear stimulator and, upon such detection, communicate with the implantable cochlear stimulator to configure the cochlear stimulation system for operation. Further, the speech processor can include one or more user controls, which can be used to configure the implantable cochlear stimulator. Once configured, the implantable cochlear stimulator can use the patient specific parameters to generate the electrical stimuli that are applied to one or more cochlea stimulating channels. When configured to use one or more parameters stored in a volatile memory, an implantable cochlear stimulator can be periodically monitored during operation. Alternatively, the implantable cochlear stimulator can be configured to notify the speech processor of any change in configuration.

SUMMARY OF THE INVENTION

The present inventor recognized the need to permanently store patient specific information, such as personalized configuration settings and individual stimulation parameters, within the internal portion of a cochlear stimulation system to reduce the amount of information transmitted to the internal portion, particularly during initialization. The present inventor also recognized the need to permanently store patient specific information within the internal portion of a cochlear stimulation system to permit recovery of the patient specific information without reference to an external storage device. Further, the need to permanently store non-patient specific information, such as one or more general parameter associated with a speech processing strategy, within the external portion of a cochlear stimulation system is recognized.

The present inventor also recognized that, although patient specific information and non-patient specific information is permanently stored, at least a portion of the patient specific information and non-patient specific information should be stored in a manner that also will allow it to be purposely altered, such as through a reprogramming operation. Additionally, the need to perform non-patient specific speech processing operations within the external portion of a cochlear stimulation system and patient specific speech processing operations within the internal portion of a cochlear stimulation system is also recognized. Further, the present inventor recognized the need to permit reprogramming of non-patient specific information, such as speech processing parameters, without necessitating the reprogramming of patient specific information. Accordingly, the techniques and apparatus described here implement algorithms for permanently storing patient specific information in an internal portion of a cochlear stimulation system, permanently storing non-patient specific information within an external portion of a cochlear implant system, and/or for performing speech processing operations within a corresponding portion of a cochlear stimulation system.

In general, in one aspect, the techniques can be implemented to include determining an item of patient specific information, transferring the item of patient specific information to an implantable portion of the cochlear stimulation system, and permanently storing the item of patient specific information in the implantable portion of the cochlear stimulation system.

The techniques also can be implemented such that the item of patient specific information comprises a parameter for use in generating a stimulation current. The techniques further can be implemented such that the implantable portion of the cochlear stimulation system is configured to permanently store one or more items of patient specific information in an alterable fashion. Additionally, the techniques can be implemented to include initializing the implantable portion of the cochlear stimulation system using one or more of the permanently stored items of patient specific information.

The techniques also can be implemented to include determining an item of non-patient specific information for use in processing a received acoustic signal and permanently storing the item of non-patient specific information in an external portion of the cochlear stimulation system, wherein the external portion comprises a speech processor. Further, the techniques can be implemented to include determining a substitute item of non-patient specific information, permanently storing the substitute item of non-patient specific information in the speech processor in place of the item of non-patient specific information, retaining the one or more items of patient specific information permanently stored in the implantable portion of the cochlear stimulation system, and generating a stimulation current using the substitute item of non-patient specific information and the one or more items of patient specific information.

The techniques also can be implemented to include replacing the speech processor with a substitute speech processor, retaining the one or more items of patient specific information permanently stored in the implantable portion of the cochlear stimulation system, and operating the cochlear stimulation system using the substitute speech processor. The techniques further can be implemented to include retrieving the item of patient specific information from the implantable portion of the cochlear stimulation system. Additionally, the techniques can be implemented to include associating a write protection with the item of patient specific information permanently stored in the implantable portion of the cochlear stimulation system. Further, the techniques can be implemented such that the associated write protection is reversible.

The techniques also can be implemented to include determining a substitute item of patient specific information, transferring the substitute item of patient specific information to the implantable portion of the cochlear stimulation system, and permanently storing the substitute item of patient specific information in the implantable portion of the cochlear stimulation system in place of the item of patient specific information.

In general, in another aspect, the techniques can be implemented to include an implantable portion comprising circuitry configured to receive an item of patient specific information and an internal memory in the implantable portion configured to permanently store the received item of patient specific information, wherein the internal memory is capable of storing one or more items of patient specific information.

The techniques also can be implemented such that the internal memory comprises one of an EEPROM, a flash EEPROM, an FRAM, and an embedded programmable non-volatile memory. Further, the techniques can be implemented to include processor electronics in the implantable portion configured to protect at least a portion of the internal memory from alteration. Additionally, the techniques can be implemented to include processor electronics in the implantable portion configured to initialize the implantable portion using one or more items of stored patient specific information.

The techniques also can be implemented to include processor electronics in the implantable portion configured to 'communicate one or more items of stored patient specific information to an external device. Further, the techniques can be implemented to include an external portion comprising circuitry configured to receive an item of non-patient specific information and an external memory in the external portion configured to permanently store the received item of non-patient specific information, wherein the external memory is capable of storing one or more items of non-patient specific information. Additionally, the techniques can be implemented to include processor electronics in the external portion configured to communicate sound data to the implantable portion, circuitry in the implantable portion configured to receive the sound data; and processor electronics in the implantable portion configured to generate a stimulation current using the sound data and one or more items of patient specific information.

In general, in another aspect, the techniques can be implemented to include initializing an implantable portion of the cochlear stimulation system using one or more items of patient specific information, wherein the patient specific information is permanently stored in the implantable portion and initializing an external portion of the cochlear stimulation system using one or more items of non-patient specific information, wherein the non-patient specific information is permanently stored in the external portion. The techniques also can be implemented to include communicating control data from the external portion to the implantable portion, wherein the control data defines a status of one or more user controls.

The techniques described in this document may be implemented to realize one or more of the following advantages. For example, the techniques can be implemented to permit storing patient specific information in an internal portion of a cochlear stimulation system. Further, the techniques can be implemented to include recovering patient specific information from the internal portion of a cochlear stimulation system. The techniques also can be implemented to permit storing non-patient specific information in an external portion of a cochlear stimulation system. The techniques further can be implemented such that only sound data is transmitted from the speech processor to the implantable cochlear stimulator, thereby reducing the amount of information that is transmitted from the external portion to the internal portion of the cochlear stimulation system. Additionally, the techniques can be implemented to reduce the frequency of or to eliminate altogether the periodic validation of patient specific information stored in an internal portion, thereby reducing the complexity of the communication link between the external portion and the internal portion of a cochlear stimulation system.

The techniques also can be implemented such that the cochlear stimulation portion can be configured as soon as the cochlear stimulation system is initialized, without having to first receive information, such as parameters, from the speech processor portion. Further, the techniques can be implemented to permit replacing the external portion of the cochlear stimulation system, including the speech processor, without replacing the internal portion of the cochlear stimulation system or requiring the patient to undergo a new fitting procedure. Additionally, the techniques can be implemented to include reprogramming the speech processor, such as with a new speech processing strategy, without requiring the patient to undergo a new fitting procedure. Also, the techniques can be implemented to permit the substitution of an existing external speech processor with an alternate external speech processor without first programming the alternate external speech processor with patient specific information and without requiring the patient to undergo a new fitting procedure.

These general and specific techniques can be implemented using an apparatus, a method, a system, or any combination of an apparatus, methods, and systems. The details of one or more implementations are set forth in the accompanying drawings and the description below. Further features, aspects, and advantages will become apparent from the description, the drawings, and the claims.

BRIEF DESCRIPTION OF THE DRAWINGS

Like reference symbols indicate like elements throughout the specification and drawings.

DETAILED DESCRIPTION OF THE DRAWINGS

Figure 1:
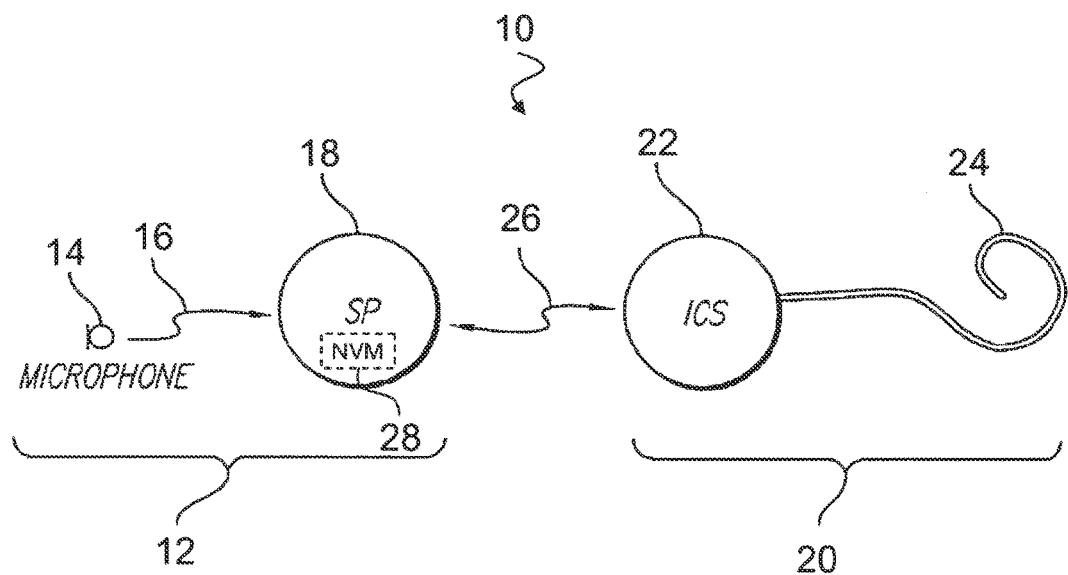
FIG. 1 is a block diagram of a cochlear stimulation system.
Figure 2A:
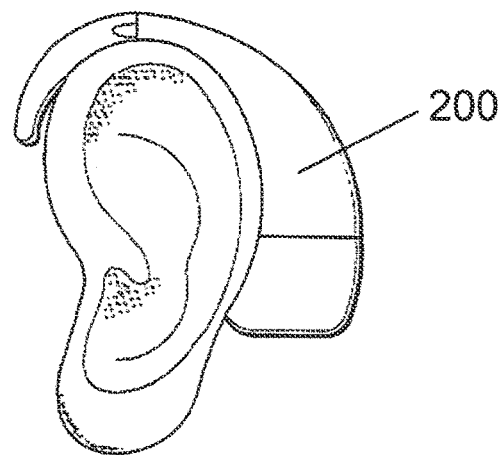
FIGS. 2A and 2B depict a behind-the-ear prosthetic device for use in a cochlear stimulation system.
Figure 2B:
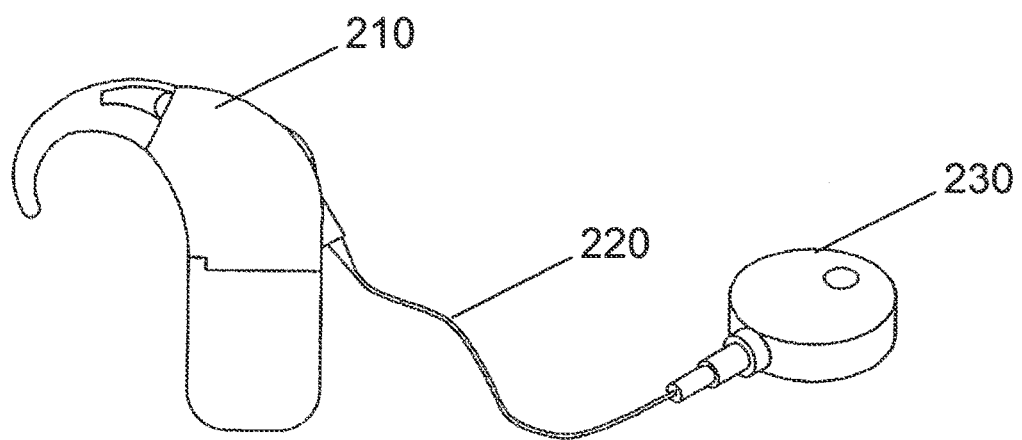

FIG. 1 presents a cochlear stimulation system 10 that includes a speech processor portion 12 and a cochlear stimulation portion 20. The speech processor portion 12 includes one or more microphones 14 and a speech processor 18. The speech processor portion 12 can be worn, placed, or attached externally to a patient. For example, the speech processor portion 12 can be incorporated into a housing that can be worn, such as the behind-the-ear prosthetic device 200 depicted in FIG. 2A or the behind-the-ear prosthetic device 210 depicted in FIG. 2B. The external portion of the communication link 26 that couples the speech processor portion 12 and the cochlear stimulation portion 20 can be included in the housing, such as in the behind-the-ear prosthetic device 200 depicted in FIG. 2A. Alternatively, as shown in FIG. 2B, a communication device 230 that comprises the external portion of the communication link 26 can be coupled to the behind-the-ear prosthetic device 210 through an interface 220. The interface 220 can be wired or wireless.

Further, the one or more microphones 14 can be included in the housing incorporating the speech processor 12 or can be situated within the outer ear, the ear canal, or the middle ear of the patient. The one or more microphones 14 can be connected directly to the speech processor 18 using a physically coupled communication link 16, such as one or more wires. Alternatively, the communication link 16 can be wireless and the one or more microphones 14 can be coupled to the speech processor 18 through an appropriate communication link 16, such as a radio frequency link or any other wireless data link capable of communicating sensed acoustic signals to the speech processor 18. In another implementation, a channel, such as a sound tube, can be located within the outer ear, the ear canal, or the middle ear of the patient in order to convey sensed acoustic information to the one or more microphones 14 included in the speech processor portion 12.

The cochlear stimulation portion 20 can include an implantable cochlear stimulator 22 and an electrode array 24, which combine to form one or more cochlea stimulating channels. Each of the cochlea stimulating channels is typically associated with an individual electrode, a pair of electrodes, or a grouping of electrodes located within or on the electrode array 24. The electrode array 24 is adapted to be implanted within the cochlea of a patient and includes a plurality of electrodes, e.g., sixteen or thirty-two electrodes, spaced along its length that are coupled to and can be selectively stimulated by the implantable cochlear stimulator 22. Electronic circuitry within the implantable cochlear stimulator 22 produces a specified stimulation current that is to be applied to selected electrodes included within the electrode array 24 in accordance with one or more items of stimulation information, e.g., processed sound data, received from the speech processor 18. The electrode array 24 may be substantially as shown and described in U.S. Pat. Nos. 4,819,647 and 6,129,753, each of which is incorporated herein by reference. Alternatively, the electrode array 24 can be any other electrode array known in the art.

The speech processor 18 and the implantable cochlear stimulator 22 can be electronically coupled through a suitable communication link 26. In an implementation, the communication link 26 can comprise a transcutaneous (through the skin) link that allows power, control data, and processed sound data to be transmitted from the speech processor 18 to the implantable cochlear stimulator 22. In another implementation, the implantable cochlear stimulator 22 also can be configured to transmit information, such as parameters and status signals, to the speech processor 18 over the communication link 26. In order to facilitate bidirectional communication between the speech processor 18 and the implantable cochlear stimulator 22, the communication link 26 can include more than one channel. Additionally, interference between the channels can be reduced or eliminated through the use of different transmission techniques. For example, information can be transmitted on a first channel using an amplitude-modulated carrier and information can be transmitted on a second channel using a frequency-modulated carrier.

The communication link 26 can be realized though use of an implanted antenna coil, such as an antenna coil included in the implantable cochlear stimulator 22, and an external antenna coil included in or coupled to the speech processor portion 12. The external antenna coil can be positioned so that it is aligned with the implanted antenna coil, allowing the coils to be inductively coupled to one another and thereby permitting power and information, e.g., stimulation signals and control data, to be transmitted from the speech processor 18 to the implantable cochlear stimulator 22. The inductively coupled coils also can be used to transmit information from the implantable cochlear stimulator 22 to the speech processor 18.

In multi-channel cochlear stimulation systems, complex stimulation patterns involving one or more sites along the cochlea can be produced in order to more accurately evoke responses representative of the different pitches that are normally present in sound. These complex stimulation patterns can be generated with respect to a plurality of factors, including frequency, pulse amplitude, and pulse width. Additionally, stimulation may be delivered to the patient in a simultaneous stimulation pattern, in which two or more electrode pairs produce stimulation at substantially the same time, or a sequential stimulation pattern, in which only one electrode pair produces stimulation at a given time. Because cochlear stimulation has become increasingly sophisticated, a cochlear stimulation system, or cochlear implant, is typically customized in one or more fitting sessions to provide individualized stimulation to the patient.

When a cochlear stimulation system, such as the cochlear stimulation system 10 depicted in FIG. 1, is first provided to a patient, an audiologist or other such specialist initially selects the modes and methods of operation that characterize the system, such as the selection of an appropriate speech processing strategy. The specialist selects the modes and methods of operation such that the cochlear stimulation system 10 will be able to best perform its intended function of helping the recipient to sense sound. Upon the selection of a speech processing strategy, the information defining the selected speech processing strategy, including operating parameters such as spatial and temporal stimulation parameters, can be customized to the needs of the patient. The operating parameters can include the duration and shape of the stimulation waveform, location information (e.g., the identification of the specific electrode or electrode grouping that is to receive the stimulation current), and timing information (e.g., when the stimulation current is to be applied to the electrode or electrode grouping). Because they are customized to meet the needs of an individual patient, the operating parameters represent a type of patient specific information.

Figure 3:
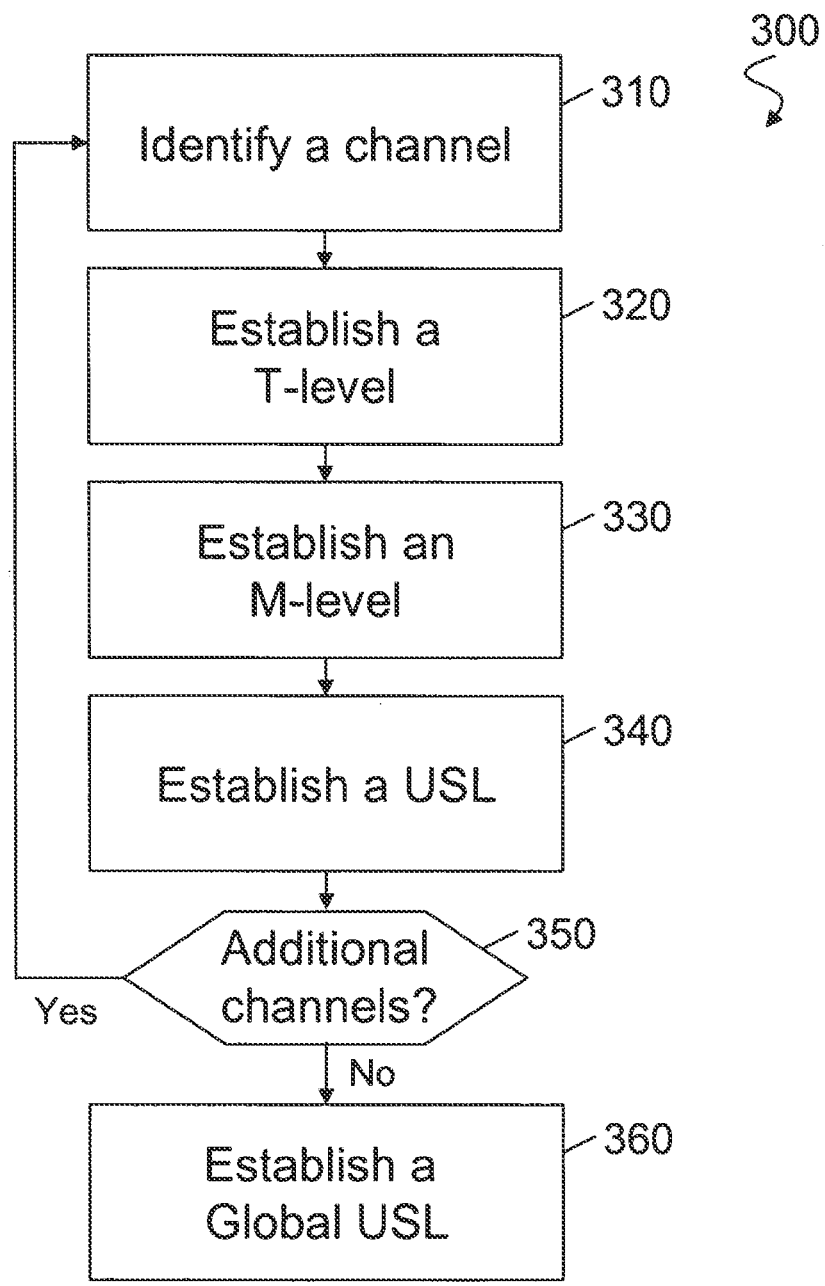
FIG. 3 is a flowchart that describes establishing one or more patient specific parameters.

FIG. 3 presents a flowchart describing a fitting session 300, during which operating parameters comprising patient specific information are selected. During the fitting session 300, thresholds and threshold values associated with one or more psychophysically-determined pseudo-comfort levels can be measured and selected. In an implementation, a cochlear stimulation channel associated with the cochlear stimulation system can be identified 310 and one or more levels associated with the identified channel can be set. For example, a minimum threshold T can be established 320 for the identified cochlear stimulation channel. The T-level represents the minimum stimulation current, which, when applied to an electrode associated with the cochlear stimulation channel produces a sensed perception of sound in the patient at least 50 percent of the time. It also is possible to establish a comfort-level threshold M 330 that corresponds to the identified cochlear stimulation channel. The M-level is a comfort level that represents a stimulation current, which, when applied to an electrode associated with the cochlear stimulation channel produces a sensed perception of sound in the patient that is moderately loud, but does not produce discomfort. Therefore, the T- and M-levels associated with one or more channels can be used by a fitting system to properly map sensed sounds to electrical stimuli (e.g., current levels) that can be perceived by the patient.

An upper stimulus level (USL) that corresponds to the identified cochlear stimulation channel also can be established 340. The USL represents the maximum stimulation current that can be applied to the one or more electrodes associated with the identified cochlear stimulation channel, which will produce a sensed perception of sound in the patient that can be tolerated. Since the M-level represents a comfortable stimulation current, the USL is typically selected such that it exceeds the M-level but does not exceed the maximum comfort level of the patient. In an implementation, the USL can be set at a level that exceeds the M-level by an arbitrary amount, such as 10 µA. Alternatively, the USL can be independently measured and established during the fitting session 300 using the response to feedback provided by the patient. After one or more of the levels associated with the identified cochlear stimulation channel have been established, it can be determined whether any cochlear stimulation channels remain for which one or more levels are to be established 350. If such an additional cochlear stimulation channel remains, the additional channel can be identified 310. Otherwise, a Global USL parameter can be established 360.

A Global USL parameter can be used to offset the individual USL parameter values corresponding to the one or more cochlear stimulation channels of the cochlear stimulation system. The Global USL parameter can be used to provide lateral movement of the input-output amplitude curve while maintaining the relative relationships between the values, wherein the input is the amplitude data of the sensed acoustic signal and the output is the amplitude of the electrical stimuli. Additionally, one or more spatial stimulation parameters and temporal stimulation parameters associated with a speech processing strategy also can be established during a fitting session 300. In another implementation, any combination of the Global USL parameter, spatial stimulation parameters, temporal stimulation parameters, and the T-level, M-level, and USL parameters associated with the one or more cochlear stimulation channels included in the cochlear stimulation system can be set or reset during a fitting session 300.

When one or more items of patient specific information have been established, such as the patient specific parameters associated with the one or more cochlear stimulation channels, the patient specific information can be transmitted to the cochlear stimulation portion 20. For example, the patient specific information can be transmitted transcutaneously over the communication link 26. Once received in the cochlear stimulation portion 20, the patient specific information can be permanently stored, such that the information is preserved even in the absence of power. In this manner, the stored patient specific information will be permanently associated with the patient.

In an implementation, the stored patient specific information also can be transmitted from the cochlear stimulation portion 20, e.g. over the communication link 26, to an external device, such as the speech processor portion 12 or a separate programming device. Retrieval of the stored patient specific information can be performed to identify the stored values, such as for verification purposes after a fitting session. If a discrepancy is detected, the storing operation can be repeated for one or more items of patient specific information to ensure that the correct information is stored in the cochlear stimulation portion 20. Other patient specific information can be transmitted and stored in the same manner at any point in time.

Figure 4:
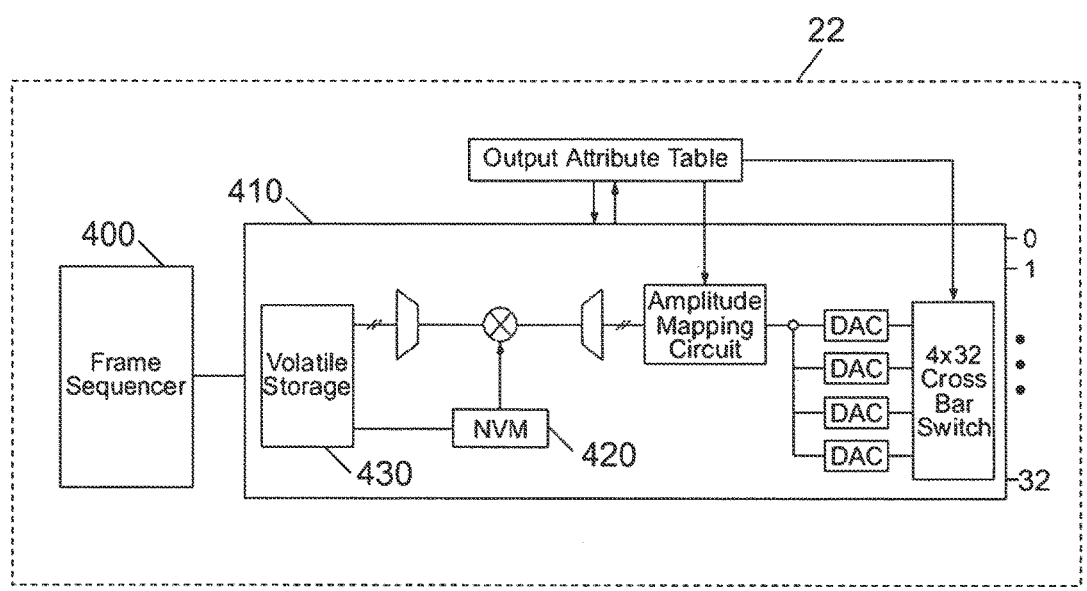
FIG. 4 is a block diagram of a portion of an implantable cochlear stimulator.

FIG. 4 presents a block diagram of an implementation of the implantable cochlear stimulator 22, through which acoustic-to-electrical amplitude mapping techniques can be implemented. The implantable cochlear stimulator 22 can include a frame sequencer 400 that is coupled to one or more channel sequencers 410 (one shown for illustration). Further, each of the one or more channel sequencers 410 can include a non-volatile memory 420, in which one or more items of patient specific information, such as individualized parameters, can be stored.

Additionally, at least a portion of the patient specific information stored in the non-volatile memory 420 can be protected against alteration, such as unintentional deletion or modification. For example, the non-volatile memory 420 can be organized to include one or more addressable locations, e.g. bytes, blocks, or pages. A write protection or other such access control mechanism can be associated with one or more of the locations of the non-volatile memory 420, which when enabled prevents the associated data from being altered. Alternatively, the ability to alter stored information can be controlled through password protection or authentication. Further, the write protection associated with a specific memory location can be implemented as a reversible protection, such as a reversible flag, or as an irreversible protection, such as a fuse or a flag that designates the location as one-time programmable. Additionally, the non-volatile memory 420 can be implemented to include any combination of reversible and irreversible write protection.

Because patient specific information can be permanently stored in the implantable cochlear stimulator 22, validation of the patient specific information during operation can be eliminated or the frequency of such validation can be reduced. Therefore, the communication link 26 between the speech processor portion 12 and the cochlear stimulation portion 20 can be simplified. Still, the patient specific information also can be stored in a manner such that any of the one or more items of patient specific information, such as a parameter, can be individually read from the non-volatile memory 420 and communicated to an external device.

In another implementation, two or more items of patient specific information can be stored in a single addressable location of the non-volatile memory 420 to efficiently utilize the available storage capacity. The non-volatile memory 420 can be implemented using any non-volatile memory known in the art, including an electrically-erasable programmable read-only memory (EEPROM), a flash EEPROM, ferroelectric random access memory (FRAM), and an embedded programmable non-volatile memory.

The implantable cochlear stimulator 22 also can include a volatile memory 430, which can be configured to store information while the implantable cochlear stimulator 22 is powered. For example, one or more items of patient specification information stored in the non-volatile memory 420 can be loaded into the volatile memory 430 for use during operation. Further, control data and processed sound data received from the speech processor 18 also can be stored in the volatile memory 430. The volatile memory 430 can be implemented using any volatile memory known in the art, including static random access memory (SRAM) and dynamic random access memory (DRAM).

With respect to FIG. 1, one or more non-patient specific parameters generally utilized by a speech processing strategy can be associated with the speech processor portion 12. As discussed above, speech processing parameters can be determined as part of the design of a speech processor, or established during the development or revision of a speech processing strategy. During operation of the cochlear stimulation system 10, one or more speech processing parameters can be used to process acoustic signals received by the one or more microphones 14. To ensure that it is readily accessible, the non-patient specific information can be permanently stored in the speech processor portion 12, such as in a non-volatile memory 28 included in the speech processor 18. In another implementation, the non-volatile memory 28 can be included in a different section of the speech processor portion 12, separate from the speech processor 18. In such an implementation, the non-volatile memory 28 can be coupled to the speech processor 18, such as by a bus or other communication pathway.

As with the implantable cochlear stimulator 22, the non-volatile memory 28 included in the speech processor 18 can be implemented using any non-volatile memory known in the art, including an electrically-erasable programmable read-only memory (EEPROM), a flash EEPROM, a ferroelectric random access memory (FRAM), an embedded programmable non-volatile memory, a programmable read-only memory (PROM), or any other such ROM. In an implementation using an alterable memory, one or more items of non-patient specific information stored in the non-volatile memory 28 of the speech processor portion 12 can be reprogrammed. Because the non-patient specific information relates only to a general speech processing strategy, and not to patient specific stimulation patterns, the non-patient specific information can be reprogrammed without reference to the patient specific information stored in the non-volatile memory 420 of the implantable cochlear stimulator 22.

It also is possible to replace the speech processor 18 included in the existing speech processor portion 12 with a compatible speech processor without requiring the patient to undergo an additional fitting procedure. If the speech processor portion 12 is contained within a single device, such a replacement may require exchanging the entire speech processor portion 12. Alternatively, the speech processor portion 12 can be configured to permit separately replacing the speech processor 18. Further, the compatible speech processor can be configured to process speech differently from the speech processor 18, such as by using a different speech processing strategy or through the use of different components. For example, the cochlear stimulation system 10 can be upgraded by replacing the existing speech processor 18 with a compatible speech processor that is configured to use an improved speech processing strategy. Alternatively, the cochlear stimulation system 10 can be upgraded by replacing the existing speech processor portion 12 with a compatible speech processor portion.

Figure 5:
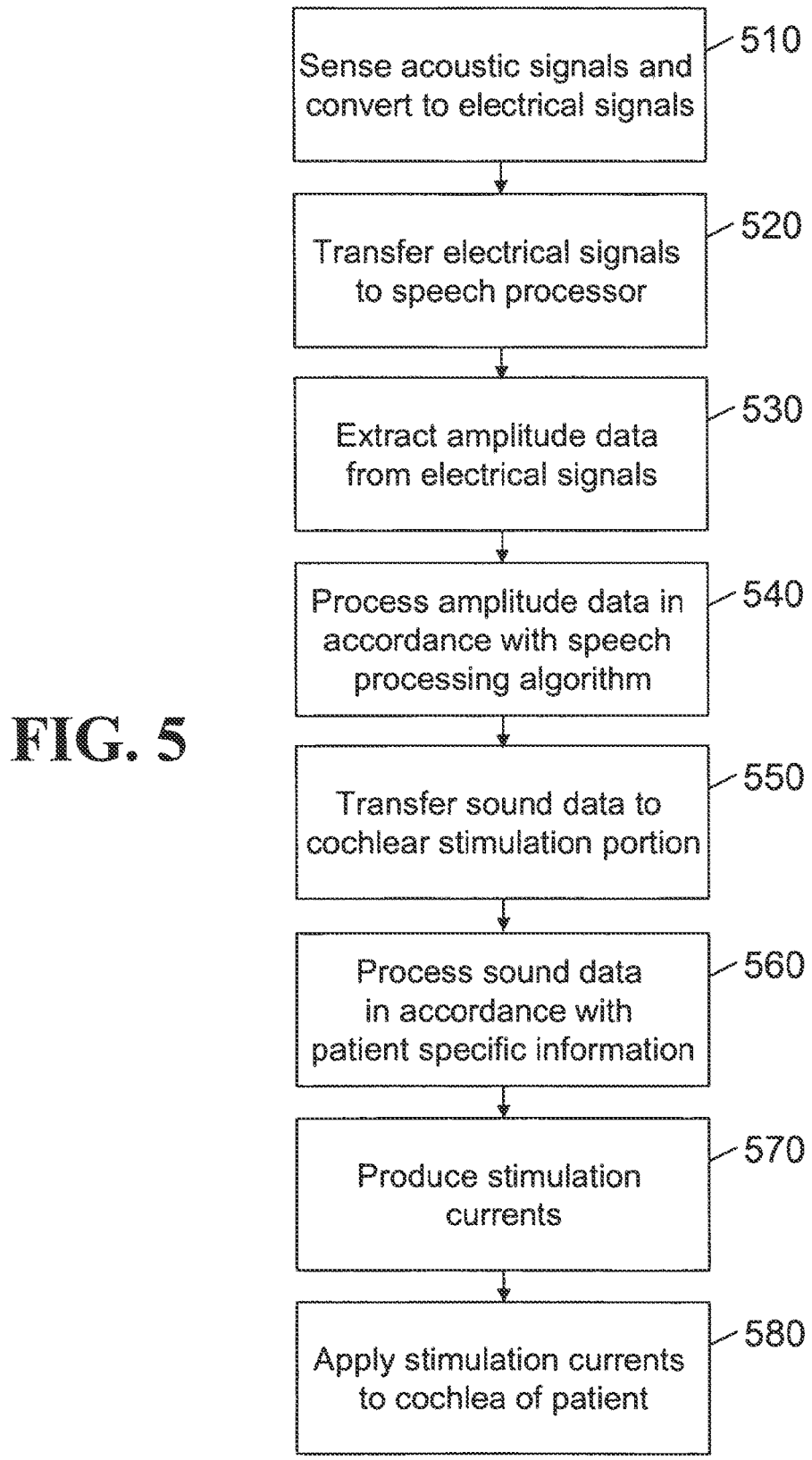
FIG. 5 is a flowchart that describes the operation of a cochlear stimulation system.

FIG. 5 presents a flowchart describing the operation of the cochlear stimulation system 10. During operation of the cochlear stimulation system 10, the one or more microphones 14 in the speech processor portion 12 can sense acoustic signals and can convert the sensed acoustic signals to corresponding electrical signals (510). The electrical signals produced by the one or more microphones 14 are provided to the to the speech processor 18 over an appropriate communication link 16, such as a circuit or wireless communication path (520). The speech processor 18 can process the received electrical signals to extract amplitude data associated with the converted acoustic signals (530). For example, the speech processor 18 can include a conventional audio front end that features automatic gain control and an analog-to-digital converter for transforming the received analog signal into digital samples that represent amplitude data. The speech processor 18 also can include one or more filters, e.g. band pass filters. Once amplitude data has been extracted from the received electrical signals, the amplitude data can be further processed in accordance with a general speech processing algorithm (540), such as an algorithm that performs operations such as filtering and noise cancellation. For example, the speech processor 18 can process the received electrical signals in accordance with one or more of the non-patient specific parameters stored in the non-volatile memory 28.

As a result of performing its portion of the signal processing operation, the speech processor 18 produces sound data in the form of one or more electrical signals that can be transmitted over the communication link 26 to the cochlear stimulation portion 20 (550). In the cochlear stimulation portion 20, the implantable cochlear stimulator 22 receives the transmitted sound data. The implantable cochlear stimulator 22 can then further process the received sound data in accordance with one or more items of patient specific information (560), such as those stored in the non-volatile memory 420.

For example, the received sound data can be processed in the implantable cochlear stimulator 22 to define the shape and duration of a stimulation waveform with respect to one or more temporal stimulation parameters and spatial stimulation parameters stored in the non-volatile memory 420. Additionally, the amplitude of the stimulation waveform can be customized for the patient based on the USL that corresponds to the associated cochlea stimulation channel. The stimulation waveform can then be converted into one or more stimulation currents (570), which are delivered to the cochlea of the patient through the electrode array 24 (580).

Figure 6:
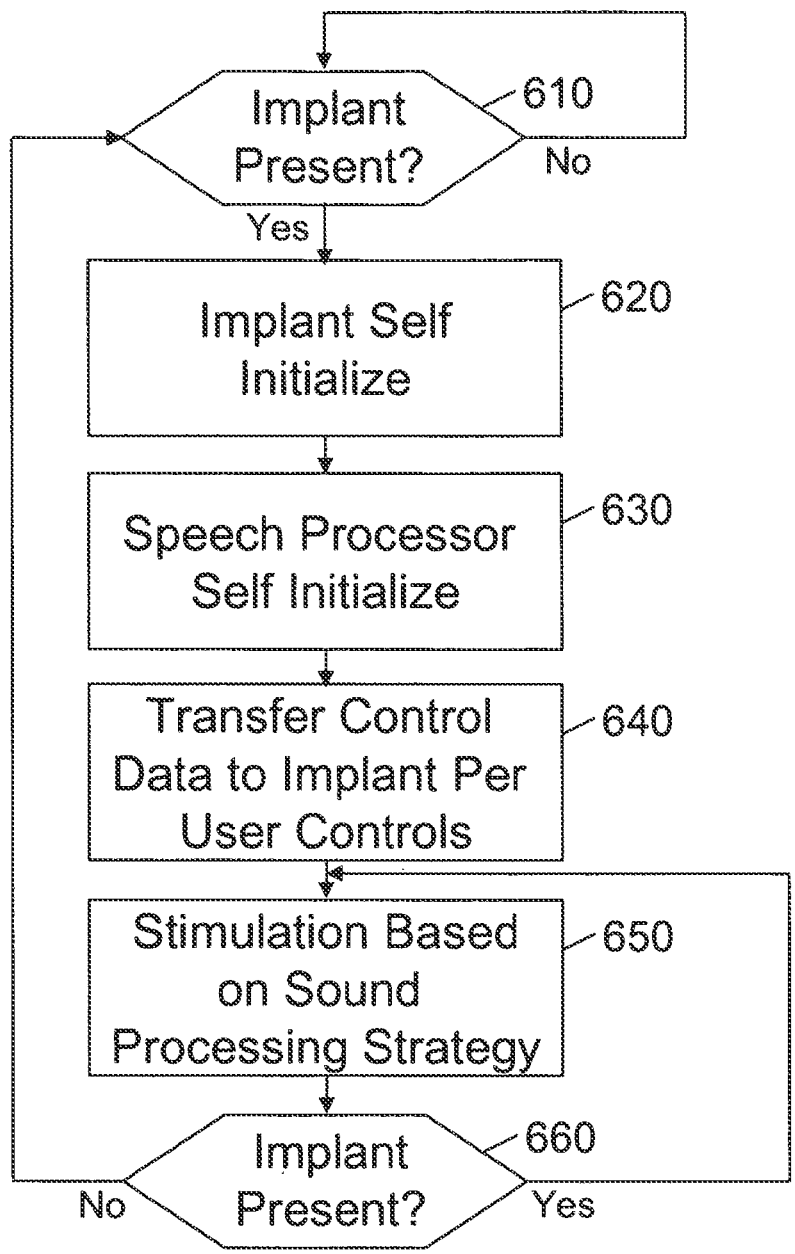
FIG. 6 is a flowchart that describes the initialization of a cochlear stimulation system.

Prior to stimulating the cochlea of the patient, the components of the cochlear stimulation system 10 must be initialized. FIG. 6 presents a flowchart describing initialization of the cochlear stimulation system 10. In an implementation, the speech processor portion 12 can be configured to provide power to and detect the presence of an implantable cochlear stimulator 22 (610). Once the implantable cochlear stimulator 22 is receiving sufficient operating power from the speech processor portion 12, the implantable cochlear stimulator 22 can execute a self-initialization process (620). The implantable cochlear stimulator 22 also can be configured to use one or more items of patient specific information stored in the non-volatile memory 420 during the self-initialization process. Additionally, the implantable cochlear stimulator 22 can be configured to perform the self-initialization process without reference to any data or other such signals from the speech processor portion 12. Therefore, the implantable cochlear stimulator 22 is not required to communicate with the speech processor portion 12 before executing the self-initialization process.

The speech processor 18 also can perform a self-initialization process, during which it can using one or more items of non-patient specific information stored in the non-volatile memory 28 included in the speech processor 18 (630). Further, the speech processor 18 can be configured to perform the self-initialization process without reference to the information stored in the implantable cochlear stimulator 22. In an implementation, the self-initialization process of the implantable cochlear stimulator 22 (620) and the self-initialization process of the speech processor 18 (630) can be performed simultaneously.

Optionally, the speech processor 18 can transmit one or more items of control data to the implantable cochlear stimulator 22 in order to define the status of one or more user controls (640), which can be included in the speech processor portion 12 to permit adjustment by the patient or a specialist. Once the self-initialization processes of the implantable cochlear stimulator 22 (620) and the speech processor 18 (630) have been completed, the speech processor portion 12 can transmit processed sound data to the implantable cochlear stimulator 22 in order to provide stimulation currents to the patient (650). Further, the speech processor portion 12 can be configured to monitor the presence and availability of the implantable cochlear stimulator 22 during operation, and to continue providing processed sound data as long as the implantable cochlear stimulator 22 is present (660). In an implementation, the speech processor portion 12 can assess the availability of the implantable cochlear stimulator periodically, so that the transfer of sound data is not interrupted.

Figure 7:
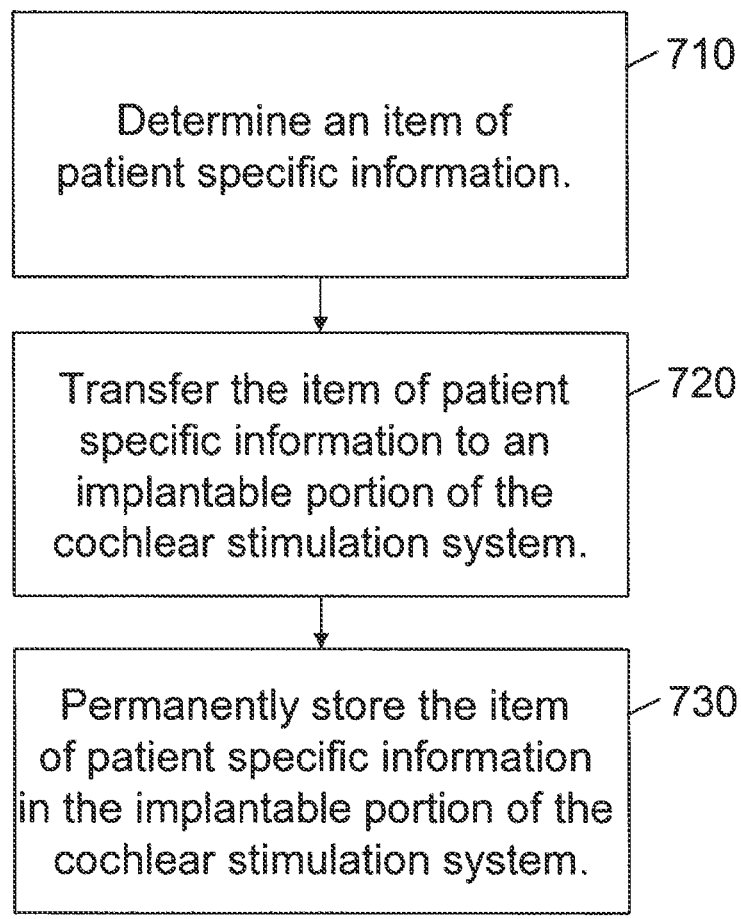
FIG. 7 is a flowchart that describes storing patient specific information in an implantable portion of a cochlear stimulation system.

FIG. 7 describes a method of storing information in a cochlear stimulation system. In a first step, an item of patient specific information is determined (710). In a second step, the item of patient specific information that was determined in the first step is transferred to an implanted portion of the cochlear stimulation system (720). Once the item of patient specific information has been transferred, a third step is to permanently store the item of patient specific information in the implanted portion of the cochlear stimulation system (730).

A number of implementations have been disclosed herein. Nevertheless, it will be understood that various modifications may be made without departing from the spirit and scope of the claims. Accordingly, other implementations are within the scope of the following claims.

The invention claimed is:

1. A method of performing neurostimulation by a cochlear stimulation system, the method comprising:
   transferring an item of patient specific information from a non-implantable speech processor of a cochlear stimulation system to an implantable neurostimulator portion of the cochlear stimulation system;
   storing the item of patient specific information in a non-volatile memory of the implantable neurostimulator portion of the cochlear stimulation system;
   initializing the implantable neurostimulator portion of the cochlear stimulation system using the item of patient specific information stored in the non-volatile memory; and
   neurostimulating a cochlear nerve with an electrical current configured from the item of patient specific information stored in the non-volatile memory,
   wherein the item of patient specific information comprises a personalized configuration setting of stimulation parameters for use by the implantable neurostimulator portion.

2. The method of claim 1, wherein the item of patient specific information comprises a parameter for use in generating a stimulation current.

3. The method of claim 1, wherein the non-volatile memory of the implantable portion of the cochlear stimulation system is configured to store the item of patient specific information in an alterable fashion.

4. The method of claim 3, further comprising:
   storing an item of non-patient specific information for use in processing a received acoustic signal in a non-volatile memory of an external portion of the cochlear stimulation system,
   wherein the external portion is wearable on a head of a patient, and
   wherein the external portion comprises a speech processor.

5. The method of claim 4, further comprising:
   storing a substitute item of non-patient specific information in the speech processor in place of the item of non-patient specific information;
   retaining the item of patient specific information stored in the non-volatile memory of the implantable portion of the cochlear stimulation system; and
   generating a stimulation current using the substitute item of non-patient specific information and the item of patient specific information.

6. The method of claim 4, further comprising:
   replacing the speech processor with a substitute speech processor;
   retaining the item of patient specific information stored in the non-volatile memory of the implantable portion of the cochlear stimulation system; and
   operating the cochlear stimulation system using the substitute speech processor.

7. The method of claim 1, further comprising: retrieving the item of patient specific information from the non-volatile memory of the implantable portion of the cochlear stimulation system.

8. The method of claim 1, further comprising: associating a write protection with the item of patient specific information stored in the non-volatile memory of the implantable portion of the cochlear stimulation system,
   wherein the write protection prevents the item of patient specific information from being altered.

9. The method of claim 8, wherein the associated write protection is reversible.

10. The method of claim 1, further comprising:
    transferring a substitute item of patient specific information to the implantable portion of the cochlear stimulation system; and
    storing the substitute item of patient specific information in the non-volatile memory of the implantable portion of the cochlear stimulation system in place of the item of patient specific information.

11. A cochlear implant system, comprising:
    an external portion;
    an implantable portion, communicatively coupled to the external portion, comprising:
      an electrode array;
      a non-volatile storage area;
      stimulation circuitry, coupled to the electrode array and the non-volatile storage area, configured for bidirectional communication with the external portion, wherein the external portion is wearable on a head of a patient;
    wherein the stimulation circuitry is configured to
      receive patient specific information from the external portion;
      store the patient specific information in the non-volatile storage area;

initialize the stimulation circuitry using the stored patient specific information without receiving information from the external portion;

generate an electrical current by the stimulation circuitry based on the item of patient specific information; and neurostimulate a cochlear nerve of the patient with the electrical current.

12. The cochlear implant system of claim 11, wherein the external portion comprises a speech processor.

13. The cochlear implant system of claim 12, wherein the speech processor is replaceable.

14. The cochlear implant system of claim 11, wherein the patient specific information comprises a parameter for use by the stimulation circuitry in generating a stimulation current in the electrode array.

15. The cochlear implant system of claim 11, wherein the non-volatile storage area is alterable.

16. The cochlear implant system of claim 11, wherein the stimulation circuitry is further configured to:

receive non-patient specific information from the external portion; and store the non-patient specific information in the non-volatile storage area.

17. The cochlear implant system of claim 11, wherein the non-volatile storage area provides reversible write protection for the patient specific information stored in the non-volatile storage area, wherein the patient specific information stored in the non-volatile storage area cannot be altered when write protected.

18. The cochlear implant system of claim 11, wherein stimulation circuitry is further configured to:

receive a substitute item of patient specific information; and store the substitute item of patient specific information in place of the patient specific information.

* * * * *